United States Patent [19]
Rheinberger et al.

[11] Patent Number: 5,780,668
[45] Date of Patent: Jul. 14, 1998

[54] X-RAY OPAQUE DENTAL MATERIALS

[75] Inventors: Volker Rheinberger, Vaduz; Norbert Moszner, Eschen, both of Liechtenstein; Ulrich Salz, Weissensberg, Germany

[73] Assignee: Ivoclar AG, Schaan, Liechtenstein

[21] Appl. No.: 450,812

[22] Filed: May 25, 1995

[30] Foreign Application Priority Data

May 30, 1994 [DE] Germany .................... 44 19 386.6

[51] Int. Cl.$^6$ .................... C07C 69/767; C07C 235/88; C07C 235/42; A61C 5/08
[52] U.S. Cl. .................... 560/113; 564/163; 564/169; 564/170; 564/176; 433/215; 433/218
[58] Field of Search .................... 560/113; 564/186, 564/187, 163, 169, 170, 176; 433/215, 218

[56] References Cited

U.S. PATENT DOCUMENTS 3,346,620 10/1967 Siggins et al. .
3,361,700 1/1968 Archer et al. .

FOREIGN PATENT DOCUMENTS 1492183 11/1969 Germany .
3521721 A1 12/1985 Germany .

OTHER PUBLICATIONS

A. Jayakrishnan and B. Chithambara Thanoo, Journal of Applied Polymer Science 44, 743–748 (1992).
Jayakrishnan, A., et al., "Synthesis and Polymerization of Some Iodine-Containing Monomers for Biomedical Applications." *Journal of Applied Polymer Science*, 44:743–48 (1992).

*Primary Examiner*—Joseph L. Schofer
*Assistant Examiner*—Wu C. Cheng
*Attorney, Agent, or Firm*—Nixon, Hargrave, Devans & Doyle

[57] ABSTRACT

X-ray opaque esters or amides of iodosubstituted benzoic acid according to formula I and polymers and dental materials produced therefrom.

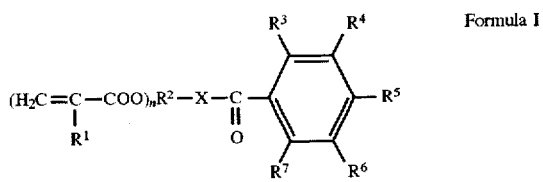

Formula I $R^1$=hydrogen or $C_1$ to $C_3$ alkyl, preferably H or $CH_3$;

$R^2$=straight-chain or branched $C_1$ to $C_6$ alkylene, oxyalkylene or arylene, preferably $C_2$ to $C_4$ alkylene and particularly preferably —$CH_2$—$CH_2$— and —$CH_2CH$(—)$CH_2$—;

X=O or NH, preferably O;

$R^3$–$R^7$=at least 3 iodine substituents, preferably in $R^3$, $R^4$ and $R^6$ or $R^3$, $R^5$ and $R^7$ position, the other groups are hydrogen, $C_1$ to $C_6$ alkyl, $C_1$ to $C_6$ alkoxy, —Cl, —Br, —OH, —$NH_2$, —N($C_1$ to $C_6$ alkyl)$_2$ or —NH—CO—($C_1$ to $C_6$ alkyl), preferably $R^3$, $R^4$, and $R^6$ are=I and $R^5$ and $R^7$=H, or $R^3$, $R^5$ and $R^7$=I and $R^4$ and $R^6$=—NH(COCH$_3$);

n=1, 2 or 3, preferably 1 or 2.

The benzoic acid esters and amides according to the invention can be well polymerized radically or anionically, the polymers are well soluble in the usual dental monomers. Dental materials produced from the monomers or polymers are characterized in that the X-ray opaque component is bonded covalently into the polymeric matrix material and cannot therefore be washed out. Furthermore, excellent X-ray opacity can be achieved without using fillers.

16 Claims, No Drawings

X-RAY OPAQUE DENTAL MATERIALS

The invention relates to X-ray opaque esters and amides of iodosubstituted benzoic acids according to formula I and polymers and dental materials produced therefrom.

Described in DE-OS 24 58 380 are X-ray opaque tooth filling compositions based on polyester resin. The X-ray opacity is achieved by adding X-ray opaque fillers. Used as fillers are glasses which contain oxides or carbonates of lanthanum, strontium, tantalum or hafnium.

DE-OS 24 20 351 relates to flowable hydrophilic tooth filling materials for root treatment which contain, as X-ray-impermeable fillers, barium sulphate, tantalum, iodoalphionic acid, iopanoic acid, ipodoic acid or bismuth subcarbonate. Hydroxyethyl methacrylate is preferably used as polymerizable monomer.

Disclosed as X-ray opaque fillers in EP-PS 0 011 735 are solid, sparingly soluble heavy metal compounds, such as barium sulphate, barium fluoride and barium silicate, bismuth, zirconium, lanthanum and thorium compounds and compounds of the rare earth metals. The use of inorganic and organic iodine compounds as X-ray contrast media is also mentioned.

Known from EP-PS 0 189 540 are dental materials which contain fluorides of the rare earth metals to achieve X-ray opacity. These fluorides are generally incorporated as powder into the dental material. A preferred compound is ytterbium fluoride.

In the aforementioned examples, the X-ray opacity of the dental materials is achieved using X-ray opaque filling materials. It is a disadvantage of these materials that the heavy metals frequently used are toxic and sometimes radioactive, whilst the oxides of the rare earths can lead to undesired discolorations of the filling or prosthesis. The transparency of the known X-ray opaque micro-filled dental materials is unsatisfactory and the high gloss polishability is inadequate. Since the X-ray opacity is in all cases realized via the filler, the production of little- or non-filled X-ray opaque dental materials, for example for fixing cements or bondings, in this way is not possible.

X-ray opaque dental materials, the X-ray opacity of which is not linked to the filler are disclosed in DE-OS 21 21 480. This publication relates to methacrylate particles in bead form which contain aliphatic halides to achieve X-ray opacity. The bead polymerizates are soluble in monomeric alkyl methacrylates and are produced by suspension polymerization in the presence of the aliphatic halogen compounds. Described as halogen compounds are bromine- or iodine-containing derivatives, iodine-containing compounds being suited exclusively in combination with bromine-containing substances. In a preferred embodiment, the bead polymerizates are dyed superficially with heavy metal compounds to increase the X-ray opacity. It is characteristic of the obtained materials that a chemical incorporation of halogen-containing end groups into the polymer takes place by chain transfer or chain termination and therefore, comparatively, only a relatively low halogen content in the polymer (below 18% by wt.) is obtainable. In the case of bromine compounds, this halogen content would lead only to weak X-ray opaque properties. Furthermore, the degree of polymerization of the polymerizates is correspondingly reduced by the chain transfer, i.e. when a high concentration of a halogen compound is used the degree of polymerization necessary for the material properties of the polymerizates cannot be achieved. Finally, in the case of a physical incorporation, the halogen compound can be washed out with organic solvents.

Moreover, materials were described which contain heavy metal organic compounds, such as for example triphenyl bismuth (Y. Delaviz, Z. X. Zhang, I. Cabasso, J. Smith, Polym. Prepr. (Amer. Chem. Soc., Polym. Div) 30 (1989) 215). These materials have the disadvantage that the heavy metal organic compounds are easily washed out of the polymeric matrix.

The use of X-ray opaque monomers containing heavy metal ions, such as zinc or barium acrylate, leads to materials which, compared with the unmodified resins, have noticeably poorer mechanical properties (K. W. M. Davey, B. E. Causton), *J. dent.* 10 (1982) 254).

Described in WO-82/01006 are X-ray opaque homo- and copolymers based on methacrylic acid esters. The X-ray opacity is achieved by covalently coupling the acrylic acid groups with X-ray-absorbing atoms. Particularly suitable for this are halogen atoms such as chlorine, bromine and iodine, bromine being preferred since chlorine is less effective and iodosubstituted polymers are too unstable. The polymers are obtained in the form of beads, crumbs, disks, rods, blocks or other forms. Only polymers, but not monomers, based on aliphatically bound halogen are described, such as for example poly (2,3-dibromopropyl methacrylate) which is obtained by expensive anionic polymerization of allyl methacrylate and subsequent bromination. X-ray opaque polymers with aromatically bound halogen which is more stable cannot be obtained in this way.

X-ray opaque, biologically degradable polyurethanes which are particularly suited for use in surgery, are known from DE-OS 41 11 914. The X-ray opacity is achieved by covalently bound X-ray contrasting agents, such as for example glycerin monoesters of triiodobenzoic acid derivatives.

Radically polymerizable iodine-containing methacrylate derivatives were also described by Brown et al. (E. Brown, M. Couturier, J. Touet; *Makromol. Chem., Rapid Commun.* 6 (1985) 503–7). The described homopolymerization of the sodium salt of 3-amino-2,4,6-triiodobenzoic acid acrylamide in aqueous solution leads however merely to a polymer with an average degree of polymerization of approx. 5. By copolymerization with N-[1,1-bis(hydroxymethyl)-2-hydroxyethyl] acrylamide or using 3-(3-acrylamidopropionamido)-2,4,6-triiodobenzoic acid, molar masses up to a maximum of 23 500 g/mol can be achieved, although these hydrophilic iodine-containing acrylamides only melt at temperatures above 260° C. and are not soluble in the usual dental monomers.

The homo- or copolymerization of 2-hydroxyethyl methacrylate ester-substituted isophthalic acid, such as for example 5-acetamido-2,4,6-triiodo-N-methylisophthalamic acid, or 2,4,6-triiodophenyl methacrylate with 2-hydroxyethyl methacrylate (HEMA) or methyl methacrylate (MMA) also leads, in the presence of azobisisobutyronitrile (AIBN) or dibenzyl peroxide (DBPO), even after 40 hours, only to oligomeric products (A. Jaykrishnan, B. C. Thanoo; *J. Appl. Polym. Sci.* 44 (1992) 743–8). 4-(1,3,6-triiodo-9-carbazoyl)- and 4-(1,3,6,8-tetraiodo-9-carbazoyl)-1-butyl methacrylates are likewise characterized only by a slight tendency towards polymerization (R. A. Minns, R. A. Gaudiana; *J. Macromol. Sci.-Pure Appl. Chem* A29 (1992) 19–30) and are therefore also not suitable for constructing an X-ray opaque polymer matrix. It is thus the object of the invention to provide monomeric X-ray opaque acrylic and methacrylic acid derivatives which can be well polymerized radically or anionically.

Another object of the invention is to provide X-ray opaque dental materials in which the X-ray opaque component is bound covalently into the polymeric matrix material and cannot therefore be washed out and which do not display the aforementioned disadvantages of known X-ray opaque filling materials. In particular, even when there is only a small amount of filler or none at all, the materials are to display a sufficient X-ray opacity and, in terms of their physical properties, be comparable with the non-X-ray opaque materials. In addition, they are to be well soluble in usual dental monomers.

It was surprisingly found that the iodosubstituted benzoic acid esters and amides according to formula I can be homo- and copolymerized very well. The polymers produced therefrom are well soluble in the usual dental monomers and, moreover, both the monomers and the polymers produced from them display a high UV stability. It is however particularly surprising that these iodine derivatives have an excellent stability and can be used to achieve the desired X-ray opacity alone, i.e. without bromine derivatives.

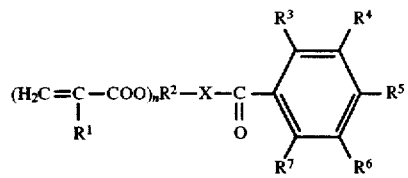

Formula I $R^1$=hydrogen or $C_1$ to $C_3$ alkyl, preferably H or $CH_3$;

$R^2$=straight-chain or branched $C_1$ to $C_6$ alkylene, oxyalkylene or arylene, preferably $C_2$ to $C_4$ alkylene and particularly preferably —$CH_2$—$CH_2$— and —$CH_2CH(—)CH_2$—;

X=O or NH, preferably O;

$R^3$–$R^7$=at least 3 iodine substituents, preferably in $R^3$, $R^4$ and $R^6$ or $R^3$, $R^5$ and $R^7$ position, the other groups are hydrogen, $C_1$ to $C_6$ alkyl, $C_1$ to $C_6$ alkoxy, —Cl, —Br, —OH, —$NH_2$, —N($C_1$ to $C_6$ alkyl)$_2$ or —NH—CO—($C_1$ to $C_6$ alkyl), preferably $R^3$, $R^4$, and $R^6$ are =I and $R^5$ and $R^7$=H, or $R^3$, $R^5$ and $R^7$=I and $R^4$ and $R^5$=—NH(COCH$_3$);

n=1, 2 or 3, preferably 1 or 2.

Preferred derivatives are the methacrylic acid esters ($R^1$= $CH_3$) of 2-hydroxyethyl ester ($R^2$=—$CH_2$—$CH_2$—) of 2,3,5-triiodo- ($R^3$, $R^4$ and $R^6$=I; $R^5$ and $R^7$=H) or 3,5-(diacetylamino)-2,4,6-triiodo benzoic acid ($R^3$, $R^5$ and $R^7$=I, $R^4$ and $R^6$=NH(COCH$_3$)). Particularlypreferred compounds are 1-(2,3,5-triiodobenzoyloxy)-and 1-(3,5-diacetylamino-2,4,6-triiodobenzoyloxy)-2,3-dimethacryloyloxypropane ($R^1$=—$CH_3$; $R^2$=—$CH_2CH(—)CH_2$—; $R^3$, $R^4$, $R^6$=I and $R^5$, $R^7$=H or $R^3$, $R^5$ and $R^7$=I, $R^4$, $R^6$=—NH(COCH$_3$) and n=2).

The X-ray opaque monomers according to the invention can be produced from triiodo- and optionally further substituted benzoic acids by reactions known from organic chemistry, such as esterification or etherification with hydroxy or halogen alkyl acrylates and methacrylates.

1-(2,3,5-triiodobenzoyloxy)-2-methacryloxyethane ($R^1$= $CH_3$; $R^2$=—$CH_2CH_2$—; $R^3$, $R^4$ and $R^6$=I; $R^5$ and $R^7$=H; n=1) can for example be obtained by reacting 2,3,5-triiodobenzoyl chloride with hydroxyethyl methacrylate and 1-(3,5-diacetylamino-2,4,6-triiodobenzoyloxy)-2,3-dimethacryloyloxypropane ($R^1$=—$CH_3$; $R^2$=—$CH_2CH(—)$ $CH_2$—; $R^3$, $R^5$, $R^7$=I, $R^4$, $R^6$=—NH(COCH$_3$), n=2) by reaction of the sodium salt of 3,5-diacetylamino-2,4,6-triiodobenzoic acid with 3-chloropropane-1,2-diol and subsequent acylation with methacrylic acid anhydride.

The amides can be produced according to methods known in organic chemistry from the acid chloride of triiodo- and optionally further substituted benzoic acid by reaction with polymerizable amides, such as e.g. acryl- or methacrylamide.

A further subject of the invention are polymers which can be obtained from the monomers according to the invention alone or by adding other X-ray opaque and/or non-X-ray opaque monomers by radical or anionic polymerization. Particularly suitable as other monomer components are mono- or polyfunctional methacrylates. Preferred comonomers are methyl methacrylate, triethylene glycol dimethacrylate, hexanediol dimethacrylate, dodecanediol dimethacrylate, bisphenol-A-dimethacrylate, bisphenol-A-glycidyl methacrylate, trimethylol propane trimethacrylate and hydroxyethyl methacrylate and urethane dimethacrylates, i.e. reaction products from isocyanates, in particular di- and/or triisocyanates with hydroxyl group-containing methacrylates. Particularly preferred are bisphenol-A-glycidyl methacrylate and the urethane dimethacrylate from hydroxyethyl methacrylate and 2,2,4-trimethylhexamethylene diisocyanate-1,6. The polymers according to the invention can be processed to give polymerizate chips or beads which can be used as fillers for dental materials. The proportion of the monomers according to the invention is typically 10 to 100% by wt., preferably 20 to 60% by wt. of the total weight of the polymers according to the invention.

Another subject of the invention are X-ray opaque dental materials which are obtained using the monomers and/or polymers according to the invention. These are suitable as filling composites, securing cements, adhesion promoters (bondings) and for the production of artificial teeth, inlays, implants, crowns, bridges and ready-made parts, preferably as tooth filling material, securing cement or bonding.

By using the dental materials according to the invention, the dentist, when preparing X-ray pictures, is able to differentiate, on the basis of the X-ray opacity, the cement or bonding layer from edge splitting which may be present.

The tooth filling materials, securing cements or bondings according to the invention contain the benzoic acid derivatives according to the invention according to formula I preferably in monomeric form. Their proportion of the total weight of the dental material depends on the desired X-ray opacity and lies in the range from 5 to 100% by wt., preferably in the range from 20 to 90% by wt. and particularly preferably in the range from 40 to 70% by wt.

The dental materials according to the invention for the production of ready-made parts such as artificial teeth, inlays, crowns, bridges, veneers and implants etc. contain the benzoic acid derivatives according to the invention according to Formula I preferably in polymerized form. Their proportion of the total weight of the dental material is inter alia dependent on the presence of X-ray opaque fillers which may be present and lies in the range from 5 to 90% by wt., preferably in the range from 10 to 70% by wt. and particularly preferably in the range from 20 to 50% by wt.

As further components, the dental materials according to the invention can also contain monomers which are suitable for copolymerizing with the monomers according to the invention. Preferred are mono- or polyfunctional methacrylates and the compounds listed as preferred above for the production of the polymers according to the invention.

Furthermore, the dental materials according to the invention can also contain polymerizates of the monomers according to the invention dissolved, suspended or soaked in dimethacrylate or another monomer.

The dental material can be cured hot, cold or by photopolymerization, depending on the type of initiator used.

Suitable as initiators for hot polymerization are the known peroxides such as dibenzoyl peroxide, dilauryl peroxide, tert.- butyl peroctoate or tert.- butylperbenzoate and azobisisobutyroethyl ester, benzpinacol and 2,2'-dimethyl benzpinacol. Dibenzoyl- and dilauryl peroxide are preferred.

Used as initiators for cold polymerization are radical-supplying systems, for example benzoyl or lauryl peroxide together with amines, such as N,N-dimethyl-sym.-xylidine or N,N-dimethyl-p-toluidine. Furthermore, compounds are also suitable which, like trimethyl silyl ketene acetals in the presence of nucleophilic catalysts or Lewis acids initiate group-transfer-polymerization of methacrylates. Preferred trimethylsilyl ketene acetals are (1-methoxy-2-methyl-1-propenyloxy)trimethyl silane and bis(1-methoxy-2-methyl-1-propenoxy)methyl silane. Preferred nucleophilic catalysts are tetrabutyl ammonium cyanide and tris(dimethylamino) sulphonium bifluoride. Preferred as Lewis acids are zinc bromide and diisobutyl aluminium chloride.

Benzophenone and benzoin and their derivatives for example can be used as initiators for photopolymerization. Furthermore, α-diketones also represent suitable photoinitiators. 9,10-phenanthrene quinone, diacetyl- or 4,4'-dichlorobenzil are preferred. Camphor quinone is particularly preferred. The α-diketones are preferably used combined with amines as reducing agents. Preferred amines are cyanoethylmethylaniline, dimethylaminoethyl methacrylate, triethanolamine and N,N-dimethyl-sym.-xylidene. The ratio of initiator to amine is generally 1:1. The most preferred photoinitiator system contains 0.3% by wt. camphor quinone and 0.5% by wt. cyanoethylmethylaniline.

When using photoinitiators, the dental materials according to the invention receive, in addition to the monomers according to the invention, preferably urethane dimethacrylate and/or bisphenol-A-glycidyl methacrylate in an amount relative to the total weight of the dental material of 0 to 95% by wt., preferably of 30 to 60% by wt., as further crosslinking component and triethylene glycol dimethacrylate in a quantity of 0 to 30% by wt. as diluting crosslinking monomer.

For use in tooth filling materials, securing cements and bondings, cold and photoinitiators are preferred, photoinitiators being particularly preferred. The radical initiators are usually used in a quantity of 0.1 to 5.0% by wt., preferably 0.3 to 2.0% by wt., relative to the total weight of the dental material.

The dental materials according to the invention can furthermore contain other added materials usual in dental chemistry, such as inorganic and organic, X-ray opaque or non-X-ray opaque added materials, such as fillers, pigmenting agents and stabilizers (cf. J. Viohl, K. Dermann, D. Quast, S. Venz, *Die Chemie der zahnärztlichen Füllkunststoffe*, Hanser-Verlag, Munich-Vienna, 1986, p. 7 et seq.).

Suitable as inorganic, non-X-ray opaque fillers are for example amorphous silicic acids. Pyrogenic or precipitated silicic acid having a BET surface area of 30 to 300 $m^2/g$ is preferred. X-ray opaque glasses, barium sulphate or ytterbium fluoride are suitable as X-ray opaque inorganic fillers. The inorganic constituents are preferably silanized in the usual way, for example with 3-methacryloyloxypropyl trimethoxysilane.

Finely particulate polymerizate chips or beads can be added as organic filling materials to the dental material. These homo- or copolymers of the usual mono- or polyfunctional methacrylates can in turn be filled with the described X-ray opaque or non-X-ray opaque inorganic fillers. They are preferably produced using the monomers and/or polymers according to the invention.

The tooth filling materials and ready-made parts such as e.g. inlays are produced according to the known processes using the monomers according to the invention (cf. inter alia EP 0 189 540 or K. Körber, K. Ludwig, *Zahnärztliche Werkstoffkunde und Technologie*, Thieme-Verlag, Stuttgart-New York 1982, p. 53 et seq.).

The invention relates not only to the X-ray opaque dental material, but also to ready-made parts produced therefrom, such as for example artificial teeth, veneers, implants, crowns, bridges, inlays etc. The invention is described in more detail with reference to the following examples.

Embodiments

Example 1

Synthesis of 2-methacyloyloxyethyl-2,3,5-triiodobenzoate (1):

A solution of 2.96 g (22 mmol) of 2-hydroxyethyl methacrylate dried over anhydrous sodium sulphate, 2.29 ml (20 mmol) anhydrous triethylamine and 0.5 g 4-dimethylaminopyridine (DMAP) in 100 ml absolute tetrahydrofuran (THF) is mixed at 0° to 5° C. dropwise with a solution of 10.69 g (20 mmol) 2,3,5-triiodobenzoyl chloride which can be obtained by reacting 2,3,5-triiodobenzoic acid with thionyl chloride (analogously to Organikum, 12th Ed. Deutscher Verlag der Wissenschaften, Berlin 1973, p.469), in 100 ml THF. The reaction mixture is kept for 40 hours at room temperature and then concentrated in a vacuum. After adding methylene chloride, the mixture is washed successively with dilute hydrochloric acid, 10% $NaHCO_3$ solution and water and then dried over anhydrous sodium sulphate. The crude product obtained by concentrating the solution is recrystallized twice from ethanol in the presence of activated charcoal; 7.5 g (59%) colourless crystals with a melting point of 99° C. which was determined using Differential Scanning Calorimetry (DSC). 1 g of the substance is compressed into a tablet (diameter approx. 12 mm, layer thickness 2 mm) and the tablet irradiated for 30 minutes with the whole wavelength range of a CPS Suntest device (Heraeus) with an irradiance strength of approx. 765 $W/m^2$. In so doing there was no discoloration of the tablet.

$C_{13}H_{11}O_4I_3$ (611.94 g/mol): Found: C 25.51 H 1.17 I 62.14 Calculated: C 25.52 H 1.81 I 62.21

$^1$H-NMR (300 MHz, $CDCl_3$, in ppm): 1.97 (s, 3H, =C($CH_3$)—); 4.49 and 4.58 (2t, 4H, —$CH_2$—$CH_2$—); 5.62 and 6.17 (2s, 2H, =$CH_2$); 7.35 and 8.31 (2s, 2H, aromat. H).

IR (film, in $cm^{-1}$): 1723 (C=O), 1639 (C=C).

Example 2

Synthesis of 2,3-dimethacryloyloxypropyl-1-(2,3,5-triiodobenzoyloxy) propane (2):

Analogous to Example 1, 5.04 g (21.9 mmol) glycerine dimethacrylate are reacted with 11.40 g (21.9 mmol) 2,3,5-triiodobenzoyl chloride in the presence of triethylamine and dimethylaminopyridine in THF. The reaction mixture is worked up as described in Example 1. 11.9 g (83.6%) of a viscous liquid are obtained. 1 g of the substance is irradiated analogously to Example 1 (layer thickness approx. 2 mm), no discoloration taking place.

$C_{18}H_{17}O_6I_3$ (710.04 g/mol): Found: C 30.8 H 2.76 I 51.10 Calculated: C 30.45 H 2.41 I 53.62

$^1$H-NMR (90 MHz, $CDCl_3$, in ppm) 1.97 (s, 3H, =C($CH_3$)—); 3.73 (m, 1H, =CH—O); 4.45 (t, 4H, —$CH_2$—O); 5.62 and 6.14 (2s, 2H, =$CH_2$); 7.67 and 8.30 (2s, 2H, aromat. H).

IR (film, in $cm^{-1}$) 1724 (C=O), 1637 (C=C).

Example 3

Synthesis of 1-(3,5-diacetylamino-2,4,6-triiodobenzoyloxy)-2,3-dimethacryloyloxypropane (3):

20 g (29 mmol) 3,5-diacetylamino-2,4,6-triiodobenzoic acid-2,3-dihydroxypropyl ester, which can be obtained from the sodium salt of 3,5-diacetylamino-2,4,6-triiodobenzoic acid by reaction with 3-chloropropane-1,2-diol at 105° C. (analogous to Organikum, 12th Edition, Deutscher Verlag der Wissenschaften, Berlin 1973, p.227 et seq.), are dissolved in 80 ml absolute pyridine and cooled to −10° C. To this solution is added dropwise 20 g (130 mmol) of commercially available methacrylic acid anhydride (Fluka) and the mixture is then stirred overnight at room temperature. The resulting clear reaction mixture is mixed with 1 l dilute hydrochloric acid and the white precipitate which forms is filtered off, washed with water to neutral and then reprecipitated from methanol/water. After drying in a fine vacuum (approx. 1 mbar, at room temperature) to a constant weight, 16.1 g (67.1%) colourless powder of amorphous appearance with a DSC melting point of 207° C. is obtained. 1 g of the substance is compressed as described in Example 1 into a tablet and irradiated; there is no discoloration.

$C_{22}H_{23}N_2O_8I_3$ (824.1 g/mol): Found: C 32.23 H 2.91 N 3.39 I 45.92 Calculated: C 32.06 H 2.81 N 3.40 I 46.19

$^1$H-NMR (300 MHz, [D$_6$]DMSO, in ppm): 1.86 and 1.87 (2s, 6H, =C(CH$_3$)—; 2.03 (s, 6H, —CO—CH$_3$); 4.34–4.55 (m, 4H, —CH$_2$—); 5.45 (m, 1H, =CH—); 5.70 and 6.05 (2s, 4H, =CH$_2$); 9.99 and 10.08 (2s, 2H, —NH—CO—).

Example 4

Solution polymerization of monomers 1, 2 and 3:

The monomers are dissolved in the concentrations given in Table 1 in swinging vessels in dimethylformamide (DMF). After adding azobisisobutyronitrile (AIBN, 40 mmol/l), the vessels are sealed and freed from oxygen in a triple freezing and thawing cycle under argon or nitrogen and then heated to 60° C. in the thermostat. Polymerization is interrupted after the times shown in Table 1 by cooling the polymerization solution in a dry ice/acetone mixture, and the polymerizate is precipitated by pouring it into an approximately 10-fold excess of methanol. The precipitate is filtered off and dried to a constant weight in a fine vacuum (approx. 1 mbar, room temperature). In the case of monomethacrylate 1, soluble homopolymers form which are precipitated from THF/methanol prior to the molecular weight determination. Table 1 shows the conversion rates and molecular weights achieved.

TABLE 1

Solution polymerization of monomers 1, 2 and 3

| Monomer | Conc. of the monomer (mol/l) | Time (min) | Conversion (%) | Molecular weight[a] $M_n \cdot 10^{-3}$ (g/mol) | Degree of polymerization $P_n = M_n M_o^{d)}$ |
|---|---|---|---|---|---|
| 1 | 1.00 | 15 | 42.1 | 146.0 | 238.6 |
| 1 | 1.00 | 30 | 68.1 | 112.3 | 183.5 |
| 1 | 1.00 | 60 | 87.5 | 86.00 | 140.5 |
| 1 | 0.50 | 60 | 73.5 | 58.9 | 96.3 |
| 2 | 0.50 | 15 | 68.7 | —[b] | — |
| 2 | 0.50 | 30 | 86.0 | — | — |
| 3 | 0.20 | 60 | 73.2 | — | — |
| 3 | 0.50 | 60 | 89.9 | — | — |
| 3 | 1.00 | 60 | 92.7 | —[c] | — |

[a] Determined by means of gel permeation chromatography (GPC) with PMMA standards
[b] Gel time: 3 minutes
[c] Gel time: 12 minutes
[d] $M_o$ = molecular weight of the monomer; $M_o$ = 611.94 g/mol for monomer 1;

Example 5

Production of X-ray opaque dental materials by copolymerization of monomers 1, 2 and 3 with conventional dental monomers:

To determine the X-ray opacity (XO) according to ISO Standard 4049 ("Dentistry—resin-based filling materials", page 1), monomers 1 and 3 according to the invention are mixed with conventional monomers and a photoinitiator in the ratios given below and the mixtures are moulded to give rods (2 mm×4 mm×25 mm), which are polymerized by irradiating twice for 3 minutes each in a light polymerization device (Spectramat, Ivoclar AG) (wavelength: 400–500 nm; light intensity: approx. 200 mW/cm$^2$). Used as photoinitiator is a mixture of camphor quinone and cyanoethylmethylaniline in a quantity of 0.3 to 0.5% by weight. Determination of the X-ray opacity was carried out by comparison with aluminium plates of the same layer thickness.

a) Monomer 3: 25% by wt.
   2-hydroxyethyl methacrylate (HEMA) 74.2%
   Initiator mixture: 0.8%
   X-ray opacity: 25% aluminium
b) Monomer 1: 23.0%
   Triethylene glycol dimethacrylate (TEGDMA): 65.7%
   Dimethylformamide: 10.5%
   Initiator mixture: 0.8%
   X-ray opacity: 100% aluminium
c) Monomer 2: 49.8%
   TEGDMA: 49.7%
   Initiator mixture 0.5%
   X-ray opacity 200% aluminium The same values for X-ray opacity (200% aluminium) are obtained when in Example c) TEGDMA is replaced by the same amounts of bisphenol-A-glycidyl methacrylate, dodecanediol dimethacrylate or the adduct from hydroxyethyl methacrylate and 2,2,4-trimethylhexamethylene diisocyanate.

We claim:

1. X-ray opaque esters or amides of iodosubstituted benzoic acid according to the formula $$(H_2C=C-COO)_n R^2 - X - C(=O) - \text{Ar}(R^3, R^4, R^5, R^6, R^7)$$
$$|$$
$$R^1$$

in which $R^1$=hydrogen or $C_1$ to $C_3$ alkyl;

$R^2$=straight-chain or branched $C_1$ to $C_6$ alkylene, oxyalkylene or arylene, X=O or NH;

$R^3$–$R^7$=at least 3 iodine substituents, and the other groups are hydrogen, $C_1$ to $C_6$ alkyl, $C_1$ to $C_6$ alkoxy, —Cl, —Br, —OH, —NH$_2$, —N($C_1$ to $C_6$ alkyl)$_2$ or —NH—CO—($C_1$ to $C_6$ alkyl);

n=1, 2 or 3 wherein said X-ray opaque esters or amides are polymerizable to produce a polymer having a molecular weight of greater than 58,900 g/mol.

2. Benzoic acid derivatives according to claim 1, characterized in that $R^1$=H or $CH_3$;

$R^2$=straight-chain or branched $C_2$ to $C_4$ alkylene;

X=O;

$R^3$, $R^4$ and $R^6$=I and $R^5$ and $R^7$ H or $R^3$, $R^5$ and $R^7$=I and $R^4$ and $R^6$=NH (COCH$_3$) and n=1 or 2.

3. Benzoic acid derivatives according to claim 1, characterized in that $R^1$=CH$_3$;

$R^2$=—CH$_2$CH$_2$— or CH$_2$CH(—)CH$_2$—;

X=O;

$R^3$, $R^4$ and $R^6$=I and $R^5$ and $R^7$=H, or $R^3$, $R^5$ and $R^7$=I and $R^4$ and $R^6$=NH(COCH$_3$) and n=1 or 2.

4. X-ray opaque dental material, characterized in that it contains at least one X-ray opaque monomer according to claim 1.

5. X-ray opaque dental material according to claim 4, characterized in that it contains 5 to 100% by wt. of the monomer or a mixture of the monomers.

6. Dental material according to claim 4, characterized in that it contains dibenzoyl peroxide and/or dilauryl peroxide as initiator for hot polymerization or that it contains benzoyl peroxide, lauryl peroxide and N,N-dimethyl-sym.-xylidine or N,N-dimethyl-p-toluidine as initiator for cold polymerization; or (1-methoxy-2-methyl-1-propenyloxy)trimethyl silane or bis(1-methoxy-2-methyl-1- propenoxy)methyl silane and tetrabutylammonium cyanide or tin bromide or tetrabutylammonium cyanide or tris(dimethylamino) sulphonium bifluoride; or that it contains a benzophenone, benzoin and/or an α-diketone as initiator for photopolymerization.

7. Dental material according to claim 6, characterized in that it contains a photoinitiator, triethyleneglycol dimethacrylate and, relative to the total weight of the dental material, up to 95% by wt. urethane dimethacrylate and/or bisphenol-A glycidyl methacrylate.

8. Dental material according to claim 7, characterized in that it contains 30 to 60% by wt. urethane dimethacrylate and/or bisphenol-A glycidyl methacrylate.

9. A method of filling teeth comprising:

filling teeth with the X-ray opaque esters or amides according to claim 1.

10. A method of bonding dental materials comprising:

bonding dental materials with the X-ray opaque esters or amides according to claim 1.

11. A dental material according to claim 4, wherein the dental material is selected from the group consisting of artificial teeth, inlays, implants, crowns, bridges, and other ready-made dental parts.

12. Benzoic acid derivatives according to claim 1, wherein X is O.

13. Benzoic acid derivatives according to claim 12, wherein said derivative is 1-(2,3,5-triiodobenzoyloxy)-2,3-dimethacryloyloxypropane.

14. Benzoic acid derivatives according to claim 12, wherein said derivative is 1-(3,5-diacetylamino-2,4,6-triiodobenzoyloxy)2,3-dimethacryloyioxypropane.

15. The benzoic acid derivatives according to claim 1, wherein n is 2 or 3.

16. The benzoic acid derivatives according to claim 1, wherein the benzoic acid derivatives are bifunctional.

* * * * *